United States Patent
Omarsson et al.

(10) Patent No.: US 9,730,814 B2
(45) Date of Patent: *Aug. 15, 2017

(54) PROSTHETIC KNEE WITH SPRING LOADED LATCH FOR PROVIDING LOCKED AND UNLOCKED CONFIGURATIONS

(71) Applicant: OSSUR HF, Reykjavik (IS)

(72) Inventors: Bjorn Omarsson, Reykjavik (IS); Sigurdur Gisli Karlsson, Kopavogur (IS); Sigurdur Olafsson, Reykjavik (IS); Gudlaugur Olafsson, Reykjavik (IS); David Landry, Quebec (CA)

(73) Assignee: OSSUR HF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 14/279,470

(22) Filed: May 16, 2014

(65) Prior Publication Data

US 2014/0249651 A1    Sep. 4, 2014

Related U.S. Application Data

(62) Division of application No. 13/484,508, filed on May 31, 2012, now Pat. No. 8,764,849.

(Continued)

(51) Int. Cl.
*A61F 2/68*    (2006.01)
*A61F 2/64*    (2006.01)
*A61F 2/50*    (2006.01)

(52) U.S. Cl.
CPC ........ *A61F 2/644* (2013.01); *A61F 2002/503* (2013.01); *A61F 2002/5003* (2013.01);
(Continued)

(58) Field of Classification Search
CPC ................ A61F 2002/6854; A61F 2/68; A61F 2/64–2/646
See application file for complete search history.

(56) References Cited

U.S. PATENT DOCUMENTS 3,533,651 A    10/1970    Prahl
3,663,967 A    5/1972    Vermillion
(Continued)

FOREIGN PATENT DOCUMENTS

DE    20 2005 019 125 U1    10/2007
GB    2004753    *  9/1977
(Continued)

OTHER PUBLICATIONS

Product Brochure: New & Improved Total Knee by Ossur 2000/1900, 2010, 2 pages, www.ossur.com.
(Continued)

*Primary Examiner* — Marcia Watkins
(74) *Attorney, Agent, or Firm* — Workman Nydegger

(57) ABSTRACT

A prosthetic knee provides security and stability, particularly to low activity users, household and limited community ambulators, single and/or slow speed ambulators, and those with little voluntary control, while also balancing walking (dynamic) performance for low activity users. The prosthetic knee includes a housing, parallel anterior links, a posterior link, and a chassis. The geometry of the links and their relationship to one another allow for low voluntary control, shortening of mid-swing, which reduces stumbling risk, and geometric stability in stance. The anterior links are particularly oriented, sized and located to provide for stability. The anterior links both extend above the posterior link and substantially below the posterior link. The prosthetic knee includes a locking mechanism arranged to arrest movement of the posterior link. The knee including a locking mechanism connected to the housing and arranged to block
(Continued)

rotation of the posterior link. The locking mechanism is a spring loaded latch including a pair of elongate springs extending downwardly from the latch to the housing and being connected to the housing below the upper pivot point of the posterior link and to a pin engaging the forward end of the latch.

5 Claims, 14 Drawing Sheets

Related U.S. Application Data

(60) Provisional application No. 61/491,707, filed on May 31, 2011, provisional application No. 61/644,117, filed on May 8, 2012.

(52) U.S. Cl.
CPC ........... *A61F 2002/5016* (2013.01); *A61F 2002/5033* (2013.01); *A61F 2002/5043* (2013.01); *A61F 2002/5073* (2013.01); *A61F 2002/5075* (2013.01); *A61F 2002/5087* (2013.01); *A61F 2002/6818* (2013.01); *A61F 2002/6854* (2013.01)

(56) References Cited

U.S. PATENT DOCUMENTS

| | | | |
|---|---|---|---|
| 3,666,299 A | 5/1972 | Butler | |
| 3,823,424 A | 7/1974 | May | |
| 3,837,010 A | 9/1974 | Prout | |
| 4,005,496 A | 2/1977 | Wilkes | |
| 4,023,215 A | 5/1977 | Moore | |
| 4,034,419 A | 7/1977 | Roberts | |
| 4,135,254 A | 1/1979 | Weber et al. | |
| 4,145,766 A | 3/1979 | May | |
| 4,685,926 A | 8/1987 | Haupt | |
| 4,911,709 A | 3/1990 | Marlow et al. | |
| 5,314,498 A | 5/1994 | Gramnas | |
| 5,704,946 A | 1/1998 | Greene | |
| 5,728,172 A | 3/1998 | Krieger | |
| 5,728,173 A | 3/1998 | Chen | |
| 5,746,774 A | 5/1998 | Kramer et al. | |
| 5,800,566 A | 9/1998 | Gramnas | |
| 5,911,709 A | 6/1999 | Hogan | |
| 5,921,358 A | 7/1999 | Gramnas | |
| 6,086,616 A | 7/2000 | Okuda et al. | |
| D439,339 S | 3/2001 | Sawatzki | |
| D446,304 S | 8/2001 | Sawatzki et al. | |
| 6,471,664 B1 * | 10/2002 | Campbell | A61F 5/0123 602/16 |
| 6,508,843 B2 | 1/2003 | Suzuki | |
| 6,706,074 B1 | 3/2004 | Chen | |
| 6,752,835 B2 | 6/2004 | Shen | |
| 6,764,244 B2 | 7/2004 | Pansiera | |
| 6,911,051 B2 | 6/2005 | Cheng | |
| D522,142 S | 5/2006 | Boiten | |
| D523,959 S | 6/2006 | Muehlenberend | |
| 7,066,964 B2 | 6/2006 | Wild | |
| D525,709 S | 7/2006 | Boiten | |
| D526,062 S | 8/2006 | Harn et al. | |
| D526,412 S | 8/2006 | Harn et al. | |
| D527,458 S | 8/2006 | Harn et al. | |
| 7,087,091 B1 | 8/2006 | Chen | |
| 7,147,667 B2 | 12/2006 | Bedard | |
| 7,195,647 B2 | 3/2007 | Chen et al. | |
| D553,741 S | 10/2007 | Chen | |
| 7,438,843 B2 | 10/2008 | Asgeirsson | |
| D592,749 S | 5/2009 | Muhlenberend | |
| 7,582,119 B2 | 9/2009 | Chen | |
| 7,618,463 B2 | 11/2009 | Oddsson et al. | |
| 7,685,926 B2 | 3/2010 | Mori | |
| 7,833,285 B2 | 11/2010 | Reinhardt | |
| 7,833,286 B2 | 11/2010 | Slemker | |
| D632,790 S | 2/2011 | Cheng | |
| 8,202,325 B2 | 6/2012 | Albrecht-Laatsch et al. | |
| 8,764,849 B2 * | 7/2014 | Omarsson et al. | 623/44 |
| 2002/0026246 A1 | 2/2002 | Suzuki | |
| 2002/0188355 A1 | 12/2002 | Chen | |
| 2006/0259153 A1 | 11/2006 | Harn et al. | |
| 2008/0281427 A1 * | 11/2008 | Shen | 623/20.29 |
| 2009/0030530 A1 | 1/2009 | Martin | |
| 2009/0143869 A1 | 6/2009 | Cheng et al. | |
| 2010/0049334 A1 | 2/2010 | Okuda et al. | |
| 2010/0094431 A1 | 4/2010 | Albrecht-Laatsch et al. | |
| 2010/0228360 A1 | 9/2010 | Pusch et al. | |
| 2010/0292807 A1 | 11/2010 | Velez et al. | |
| 2011/0009981 A1 | 1/2011 | Okuda et al. | |
| 2011/0270415 A1 | 11/2011 | Chen et al. | |
| 2012/0330440 A1 | 12/2012 | Chen et al. | |

FOREIGN PATENT DOCUMENTS

| | | |
|---|---|---|
| GB | 2 134 392 A | 8/1984 |
| JP | H03-30763 A | 2/1991 |
| SU | 1109153 A1 | 8/1984 |
| WO | 2008/072095 A2 | 6/2008 |

OTHER PUBLICATIONS

Product Brochure: Total Knee System Adjustment, Dec. 1, 2008, 2 pages, www.ossur.com.
International Search Report and Written Opinion Issued in PCT/US2012/040099, Aug. 27, 2012.
International Search Report from Corresponding PCT Application No. PCT/US2013/035432, Sep. 10, 2013.
Product Catalog: Uniprox Product Catalogue, 2010, Prosthetic Components, Orthoses and Materials. Ossur Americas Foothill Ranch, CA, 2010, 8 pages, www.ossur.com, www.uniprox.de.
Product Brochure: Rheo Knee, Walk Your Way, 2011, 20 pages, www.bionics.ossur.com.

\* cited by examiner

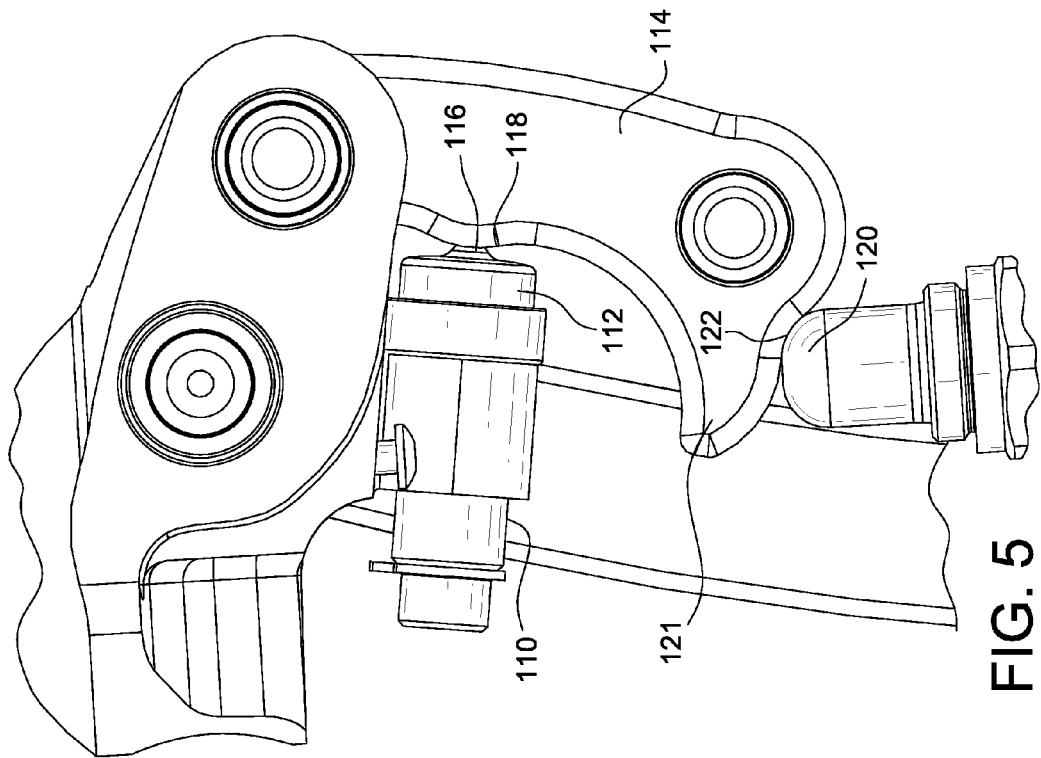
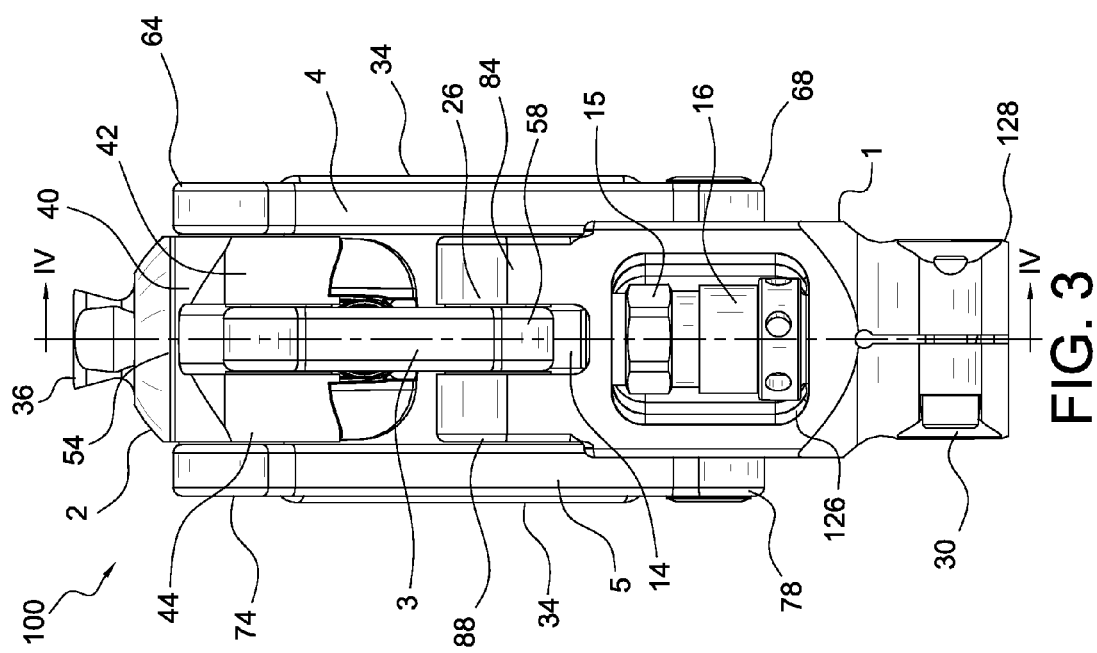

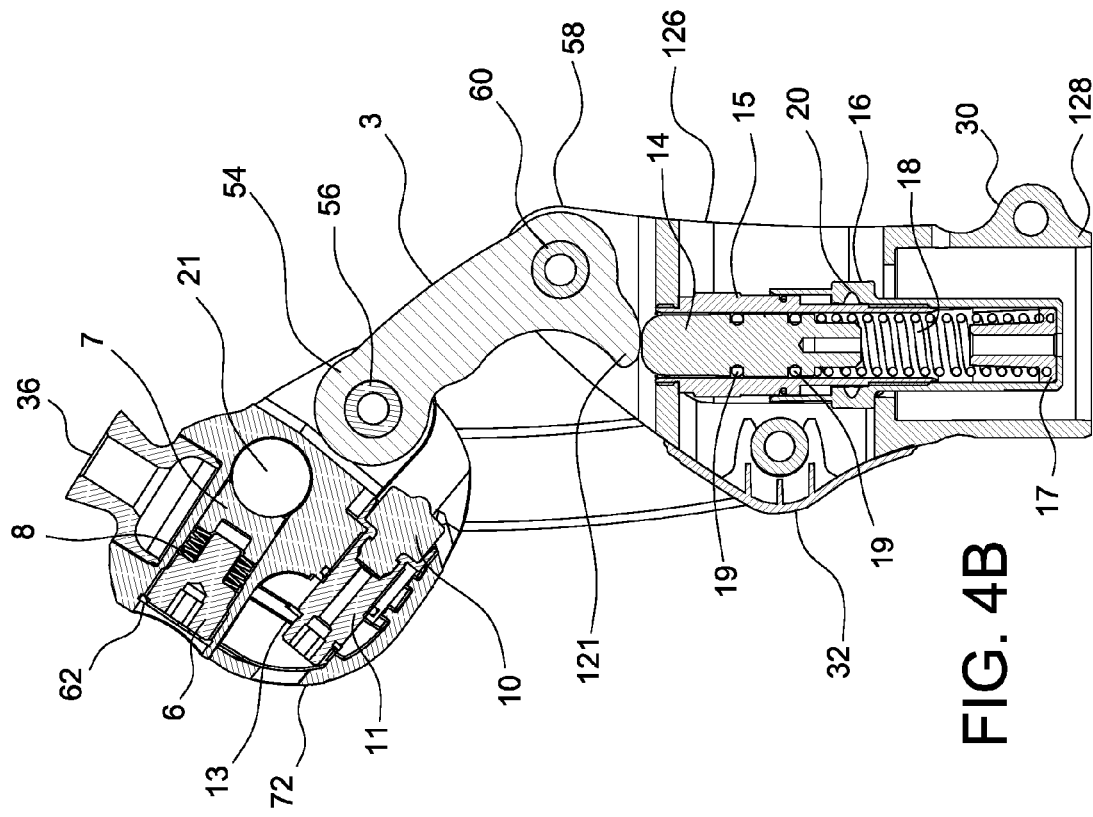
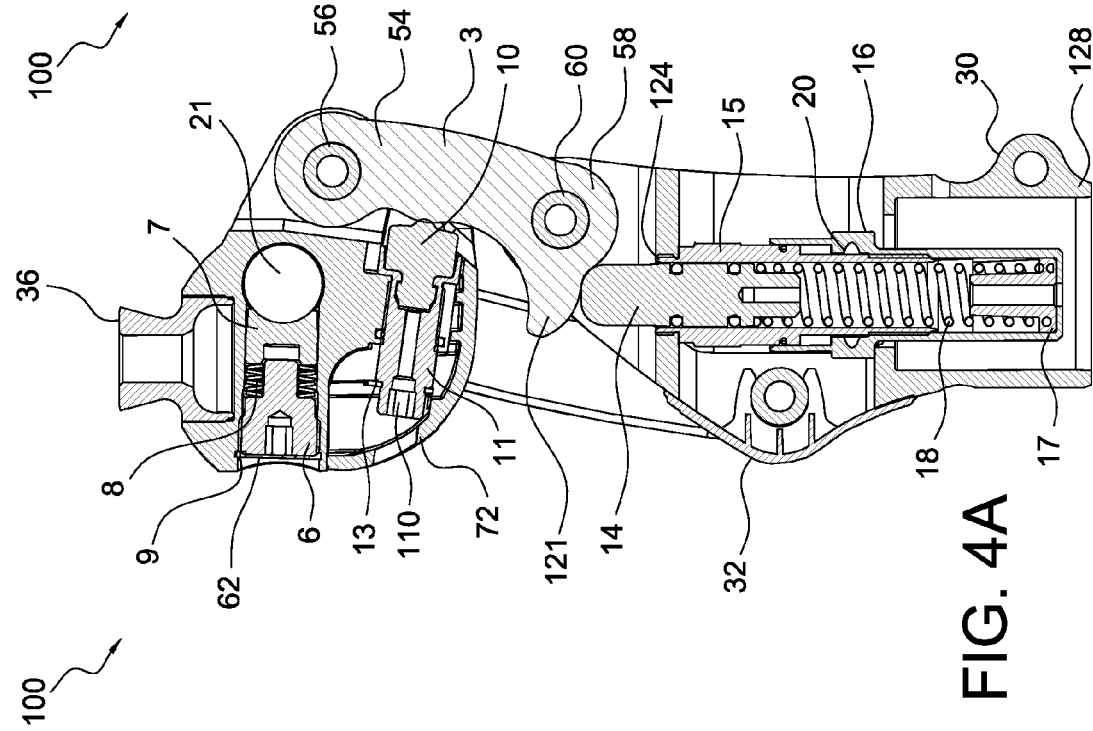

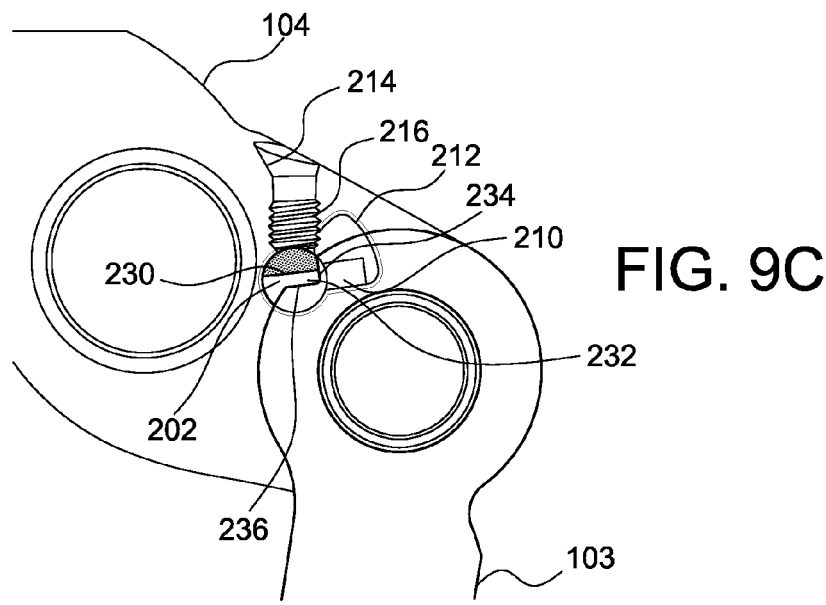
FIG. 9C
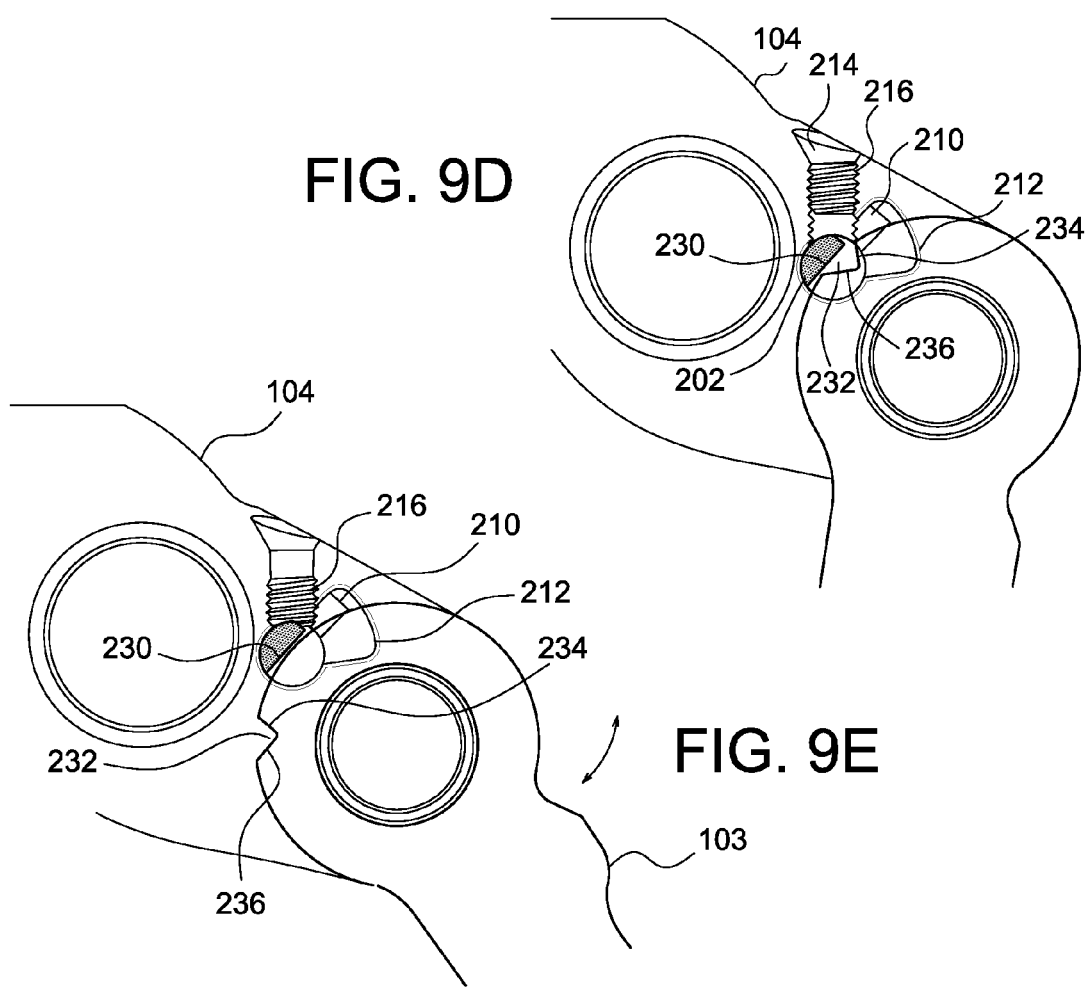
FIG. 9D
FIG. 9E

PROSTHETIC KNEE WITH SPRING LOADED LATCH FOR PROVIDING LOCKED AND UNLOCKED CONFIGURATIONS

CROSS-REFERENCE TO RELATED APPLICATIONS

This application is a divisional of U.S. Pat. No. 8,764,849, filed May 31, 2012, which claims the benefit of priority from U.S. Provisional Application No. 61/491,707, filed May 31, 2011, and U.S. Provisional Application No. 61/644,117, filed on May 8, 2012. This application incorporates by reference the entirety of U.S. Provisional Application Nos. 61/491,707 and 61/644,117.

FIELD OF THE INVENTION

The invention relates to a prosthetic knee, and more particularly to a prosthetic knee including a four bar geometry.

BACKGROUND

Artificial limbs, including leg prostheses, employ a wide range of technologies to provide solutions suitable to many differing needs. For a trans-femoral amputee, basic needs in a leg prosthesis include stability, while standing and during the stance phase of a walking gait, and mechanical compatibility with the walking (or running) gait and some manner of knee flexion during stance and swing phases of a gait.

Certain trade-offs exist between security and stability and walking or running performance (dynamic behavior). A simple, non-articulable leg (having no movable knee), for example, may provide maximum stability but does not provide for an ideal gait. Also, sitting may be awkward if a person cannot bend his knee.

For low activity users, such as the elderly or persons with other illnesses, the focus is generally more on providing security and stability than on providing walking or running performance.

SUMMARY

Accordingly, a prosthetic knee is disclosed herein that provides security and stability, particularly to low activity users, household and limited community ambulators, single and/or slow speed ambulators, and those with little voluntary control, while also balancing walking (dynamic) performance for low activity users. Thus, the disclosed prosthetic knee controls the trade-off between stability and dynamic behavior. In particular, the disclosed prosthetic knee provides, among other benefits, a good balance between stability at heel strike and ease of swing initiation.

The prosthetic knee may be used to deliver security and stability to amputees, particularly low activity amputees. The prosthetic knee is a multi-axial knee having stability adjustment to optimize the balance between knee stability and dynamic behavior for each individual user. The prosthetic knee allows for easy kneeling and sitting, and features increased toe clearance due to mid-swing shortening. Mid-swing shortening also allows the prosthesis to swing more easily through each step and helps prevent hip hiking.

The adjustment features of the prosthetic knee (including the adjustable friction, adjustable stability, and adjustable extension assist) can all be accessed externally with no disassembly of the prosthesis required. Thus, a Certified Prosthetist and Orthotist (CPO or clinician) can match and adjust the prosthetic knee to the individual user. Specifically, the CPO can adjust the extension assist mechanism to match a user's fixed walking speed and can adjust the applied friction in order to prevent excessive heel rise and terminal impact. The adjustable stability features thus lower stumbling risk, and provide good stability at heel strike.

Further, extension assist is provided in the range of 0 degrees to 70 degrees, and the amount of extension assist is easily adjusted by the CPO without removing the prosthesis from the user's residual limb.

Additionally, the dynamic behavior of the prosthetic knee, which may initially be adjusted to be low, can be increased higher as the user's confidence in using the prosthetic knee increases.

The large range of adjustability of the stability of the disclosed prosthetic knee also provides compensation for anterior/posterior offset problems in the socket used to secure the prosthetic knee to the user's residual limb.

The disclosed prosthetic knee also provides excellent knee flexion (140 degrees, or 180 degrees without the socket attached) to aid with the user's ability to sit or kneel.

According to an embodiment of the disclosure, a prosthetic knee includes a pair of anterior links, and a posterior link. The pair of anterior links preferably has a length greater than a length of the posterior link. The prosthetic knee also includes a housing connecting the pair of anterior links and the posterior link and a chassis connecting the pair of anterior links and the posterior link. The anterior link connects to the housing at first upper pivot points, and the posterior link connects to the housing at second upper pivot points, whereas the anterior link connects to the chassis at first lower pivot points, and the posterior link connects to the chassis at second lower pivot points.

The prosthetic knee may include a stability adjustment mechanism accessible from a front side of the housing. The stability adjustment mechanism has a stop element extending from a rear side of the housing and engageable with the posterior link between the second upper and lower pivot points. The stop element may define a rounded tip defining a consistent and smooth surface contact for the posterior link to strike, thereby easing use of the prosthetic knee as it enters maximum extension and reducing any noise or impact.

The prosthetic knee also may have a friction adjustment mechanism accessible from the front side of the housing, and cooperating with the pair of anterior links at the first upper pivot points. The friction adjustment mechanism preferably defines a friction adjustment screw adjustable from the front side of the housing and cooperating with a friction pad engageable with a friction shaft adapted to adjust friction at the first upper pivot points.

Likewise, the prosthetic knee may further comprise an extension assist mechanism extending from the chassis toward and engageable with a posterior link cam. The extension assist mechanism may have an extension spring extending from a bottom portion of the chassis and carry an extension assist piston engaging the posterior link cam. The posterior link cam may extend beyond the second lower pivot point toward the front side of the housing.

The prosthetic knee may further include a locking mechanism that connects to the housing and arranged to arrest movement of the posterior link near or at the second upper pivot point. The locking mechanism is pivotable on the housing and biases toward the posterior link to engage therewith. The posterior link preferably has a notched portion engageable with the locking mechanism, and at least one spring biases the locking mechanism toward the posterior link. The locking mechanism may also include a block element mountable on the locking mechanism which prevents engagement of the locking mechanism with the posterior link.

The prosthetic knee has a four bar geometry which provides for improved stability. The geometry and size relationships of the various links and pivot points are selected for greatest toe clearance, improved stability, and ease of swing initiation and improved maximum flexion. If the selection of the length of the links is to make them too long, then this may be poor for leg torsion, whereas if the links are too short, they are difficult to fit. In accordance with the improved geometry of the prosthetic knee, for example, the anterior links are preferably substantially longer than the posterior link, such that a distance between the first and second upper pivot points is on an order of 2.0-3.0 and a distance between the first and second lower pivot points is on an order of 5.2-6.2. Various other geometrical configurations are provided which achieve the desired traits of a prosthetic knee.

The numerous other advantages, features and functions of embodiments of a prosthetic knee are readily apparent and better understood in view of the following description and accompanying drawings. The following description is not intended to limit the scope of the prosthetic knee, but instead merely provides exemplary embodiments for ease of understanding.

BRIEF DESCRIPTION OF THE DRAWINGS

These and other features, aspects, and advantages of the present invention will become better understood with regard to the following description, appended claims, and accompanying drawings where:

FIG. 3 is a rear view of the prosthetic knee shown in FIG. 1;

FIGS. 4A and 4B are cross sectional views of the prosthetic knee taken along line 4-4 in FIG. 3, and showing the prosthetic knee at 0 degrees of flexion and at roughly 30 degrees of flexion, respectively;

FIG. 5 is a detailed view of the posterior link of the prosthetic knee shown in FIG. 1;

FIG. 9C is a detailed view showing the mechanism of FIG. 9A in a locked configuration.

FIG. 9D is a detailed view showing the mechanism of FIG. 9A in a position between locked and unlocked configurations.

FIG. 9E is a detailed view showing the mechanism of FIG. 9A in an unlocked configuration.

Figure 1A:
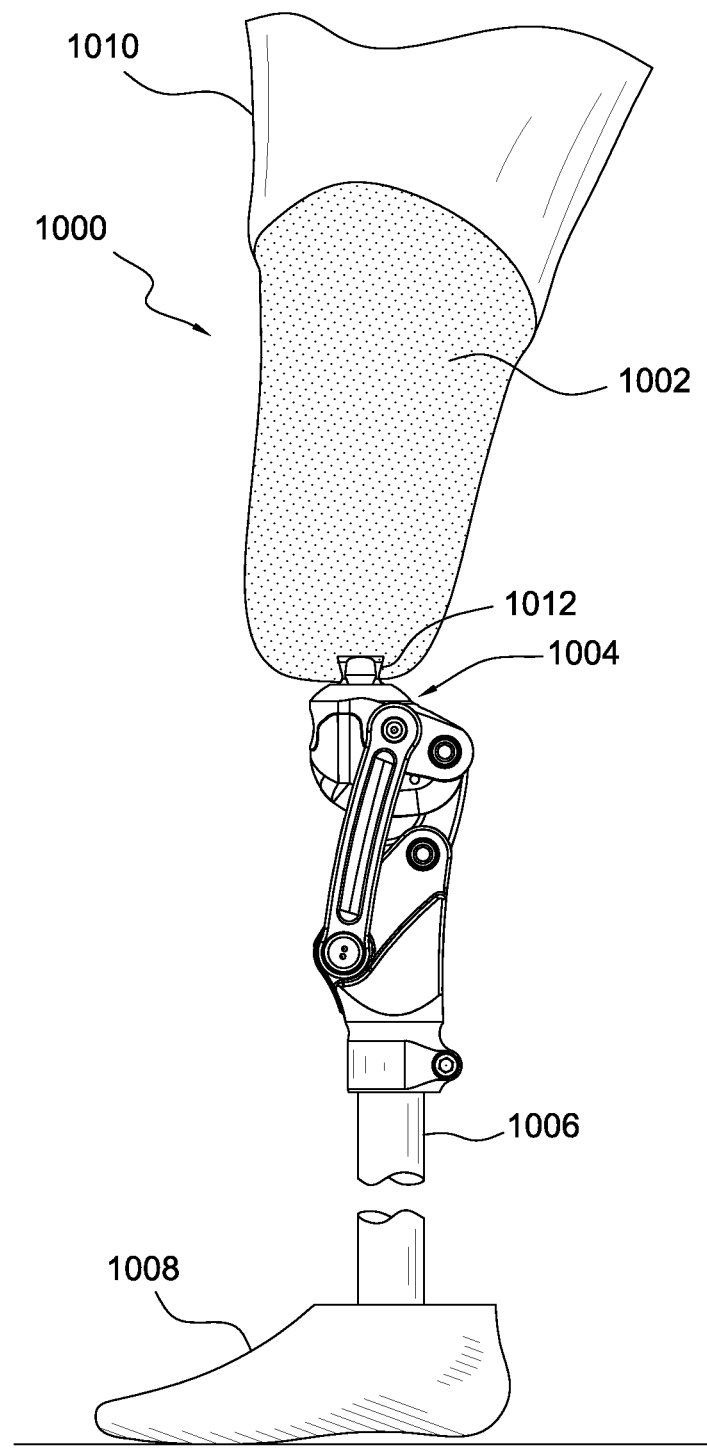
FIG. 1A is a schematic view showing a prosthetic leg and foot assembly.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary embodiments of a prosthetic knee and the components thereof, and in no way limit the structures or configurations of prosthetic knee and components thereof according to the present disclosure.

DETAILED DESCRIPTION

A. Environment and Context

FIG. 1A schematically depicts a prosthetic leg and foot assembly 1000 for a residual limb 1010. The assembly 1000 includes a socket assembly 1002 that embraces the residual limb 1010, a prosthetic knee 1004 connected to the socket assembly 1002 by an adapter 1012, a pylon 1006 connecting the knee 1004, and a foot 1008 connecting to the pylon 1006.

In order to understand the operation of the prosthetic knee described herein, a basic discussion of the gait cycle is required. A gait cycle defines the movement of the leg between successive heel contacts of the same foot. The gait cycle has two phases: stance and swing. The stance phase has three time periods: heel-strike, mid-stance and toe-off.

At some point during mid-stance, the knee joint will be at full extension. An actual knee joint will have some flexion between heel-strike and mid-stance and between mid-stance and toe-off. This is called "stance flexion." Not all prosthetic joints provide for stance flexion, and for those that do, they are either mechanically complex, expensive, or both. Moreover, these prosthetic joints typically require frequent maintenance and replacement. Additionally, the amount of stance flexion required can vary from user to user, while most prosthetic joints have no adjustability.

Maximum flexion of the knee joint, while walking, will occur at the end of the toe-off phase. The amount of maximum flexion is typically determined in part by the speed at which a person is walking. The faster a person walks the greater the amount of maximum flexion, while the slower a person walks, the lesser amount of maximum flexion. In a natural knee, the amount of maximum flexion can be controlled and limited via the musculature of the leg. In a prosthetic knee joint, some artificial means of controlling and limiting the amount of maximum flexion are typically provided. Immediately following the end of the toe-off phase begins the swing phase.

While the stance phase has three time periods, the swing phase has two time periods: acceleration and deceleration. The acceleration phase begins immediately following the maximum flexion during the toe-off phase. During the acceleration phase, the lower portion of the leg, consisting of the shin and foot, begins to swing back towards full extension. In a natural knee joint, a deceleration phase follows the acceleration phase, during which the lower portion of the leg continues to swing towards full extension. Some prosthetic joints do not provide for any deceleration during the swing phase. Other prosthetic joints provide deceleration by using costly and bulky hydraulic or pneumatic cylinders. The amount of deceleration required can vary from user to user, while most prosthetic joints have no adjustability.

For further ease of understanding the joint disclosed herein, a description of a few terms is necessary. As used herein, the term "upper" has its ordinary meaning and refers to a location that is above, or higher than another location. Likewise, the term "lower" has its ordinary meaning and refers to a location that is below, or underneath another location. The term "posterior" also has its ordinary meaning and refers to a location that is behind or to the rear of another location. The term "anterior" has its ordinary meaning and refers to a location that is ahead or to the front of another location. Lastly, the terms "left" and "right" have their ordinary meaning and as used herein refer to the left and right sides when viewing the prosthetic knee from the anterior side.

B. Exemplary Embodiment

Figure 1:
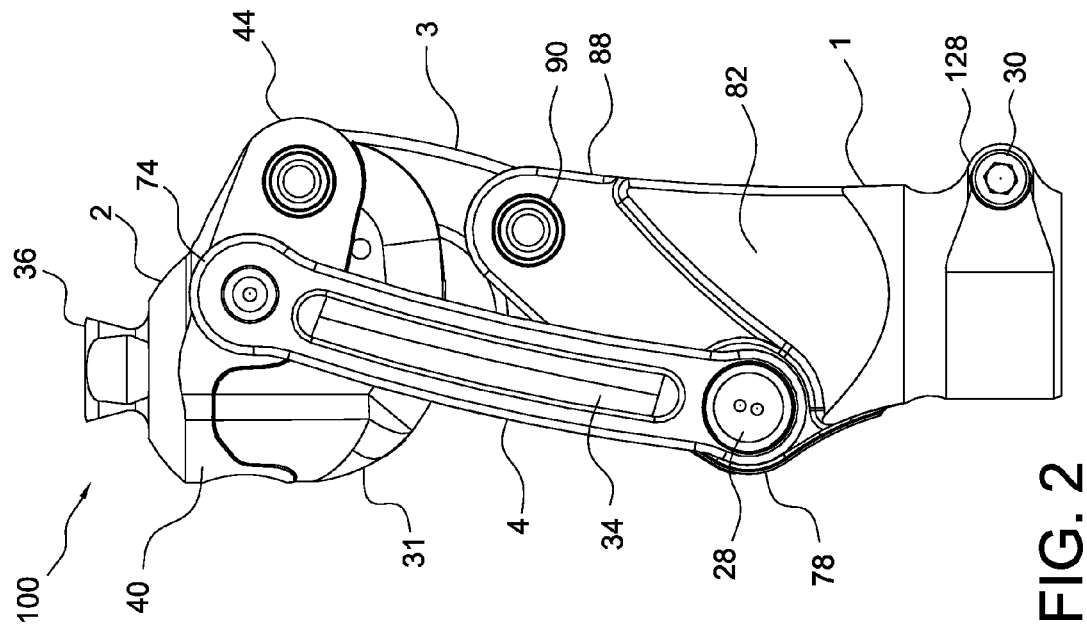
FIG. 1 is a front perspective view of a prosthetic knee according to an embodiment of this disclosure.
Figure 2:
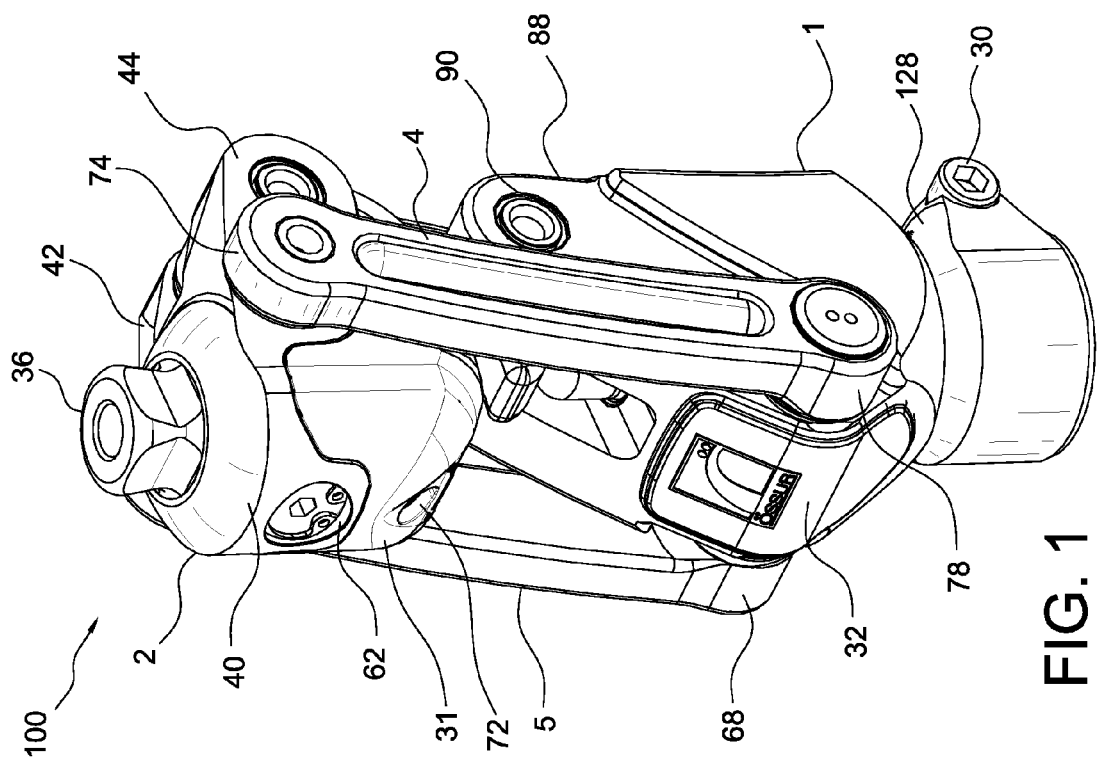
FIG. 2 is a right side view of the prosthetic knee shown in FIG. 1.

An exemplary embodiment of a prosthetic knee 100 is shown in FIGS. 1 and 2. As shown, the prosthetic knee includes a housing 2, parallel anterior links 4, 5, a posterior link 3, and a chassis 1. The prosthetic knee 100 includes a pyramid adapter 36 at the top (or a 4-prong adapter) and a distal tube clamp attachment 128, having a socket head cap screw (SHCS) 30 for tightening, at the bottom. The geometry allows for low voluntary control, shortening of mid-swing which reduces stumbling risk, and geometric stability in stance.

The anterior links 4, 5 are particularly oriented, sized and located to provide for stability. Of particular note, the anterior links 4, 5 both extend above the posterior link 3 and substantially below the posterior link 3. However, the anterior links 4, 5 are not too long for this leads to poor torsion whereas the anterior links 4, 5 are not too short for this makes it difficult to fit the prosthetic knee 100. Preferably, the anterior links 4, 5 are relatively longer than in most if not all prosthetic knees which allow for increased or longer stability in a stance phase and which is particularly beneficial to low activity users.

In addition to the selection of the length of the links as parameters for designing the knee, both the flexion factor (i.e., large angle of locking and easy swing initiation) and a large flexion angle, which allow for adapter clearance at 130 and 140 degrees, are taken into consideration. Additional parameters include locating the links for the greatest toe clearance, good stability, ease of swing initiation, and good maximum flexion for both the clamp attachment and pyramid adapter.

Figure 2B:
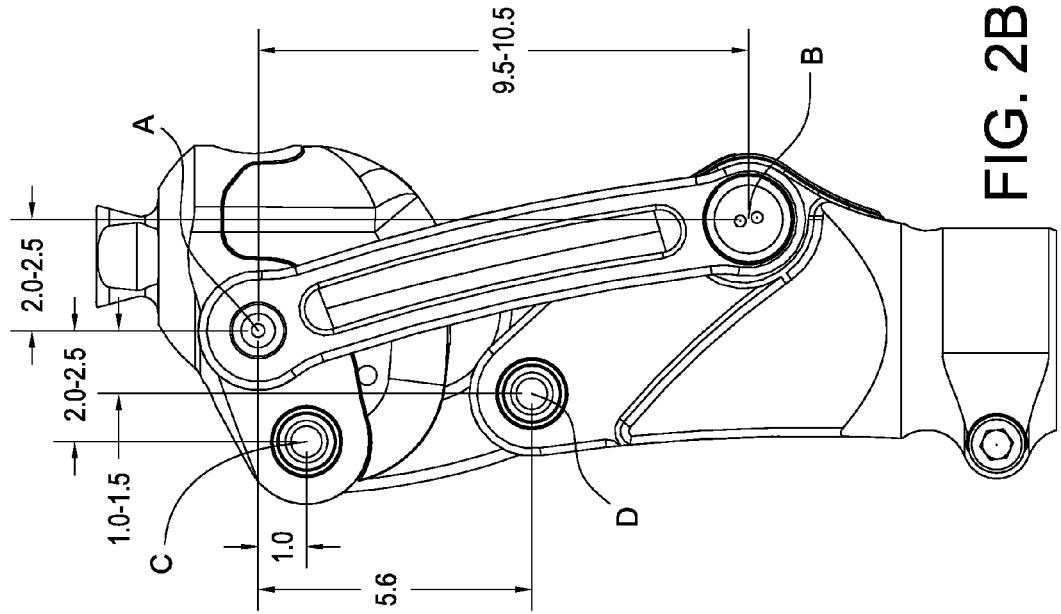
FIGS. 2A and 2B are left side views of the prosthetic knee shown in FIG. 1 and illustrating the various ratios of locations among the pivot points and the lengths of the links relative to one another.
Figure 2A:
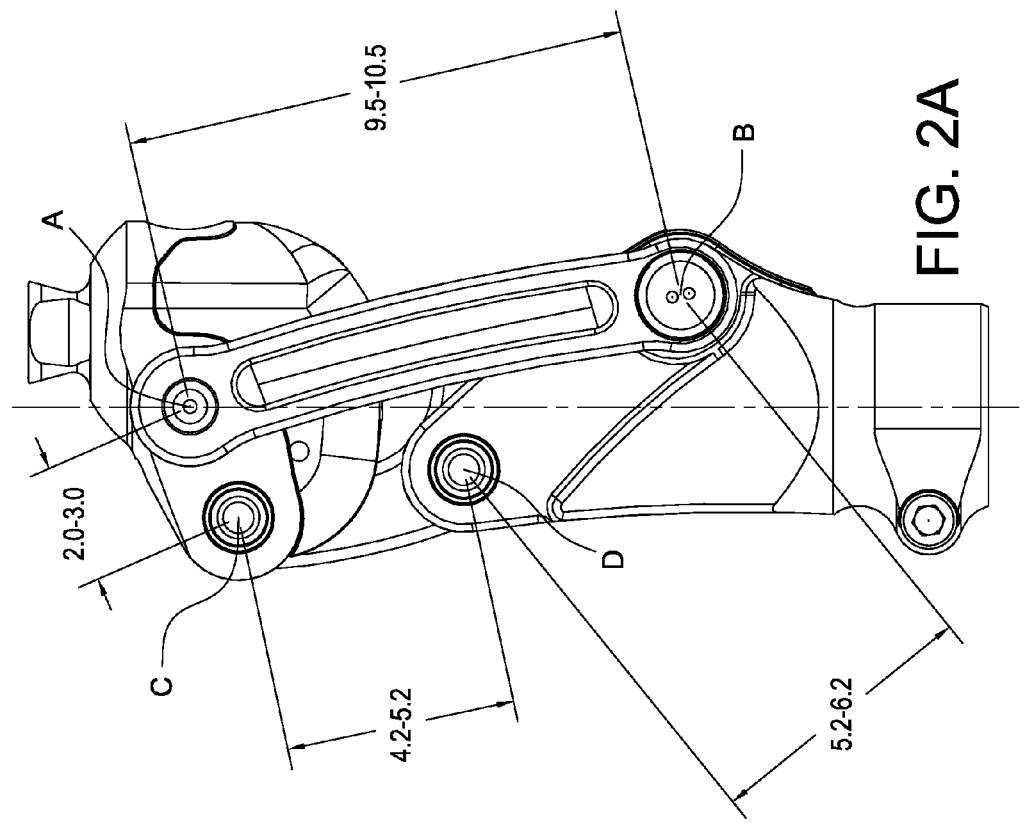

In regard to the spatial relationship among the components of the prosthetic knee, FIGS. 2A and 2B exemplify that the upper anterior pivot point A at 0 degrees extension is in the same frontal/coronal plane as the tube clamp attachment 128. This arrangement provides significant stability to the prosthetic knee and hence the wearer of the knee.

FIGS. 2A and 2B also show the ranges of various ratios of locations among the pivot points A, B, C, D and the lengths of the links relative to one another, taking 1.0 as the base number (representing the vertical distance between the upper anterior pivot point A and the upper posterior pivot point C). The vertical distance between the upper anterior pivot point A and the lower anterior pivot point B is in the range of 9.5-10.5, and the vertical distance between the upper anterior pivot point A and the lower posterior pivot point D is in the range of 5-6. Particularly, the relative locations of the links and their positions relative to attachments in the form of the pyramid adapter and the clamp attachment determine their geometry and spatial relationships.

Figure 7:
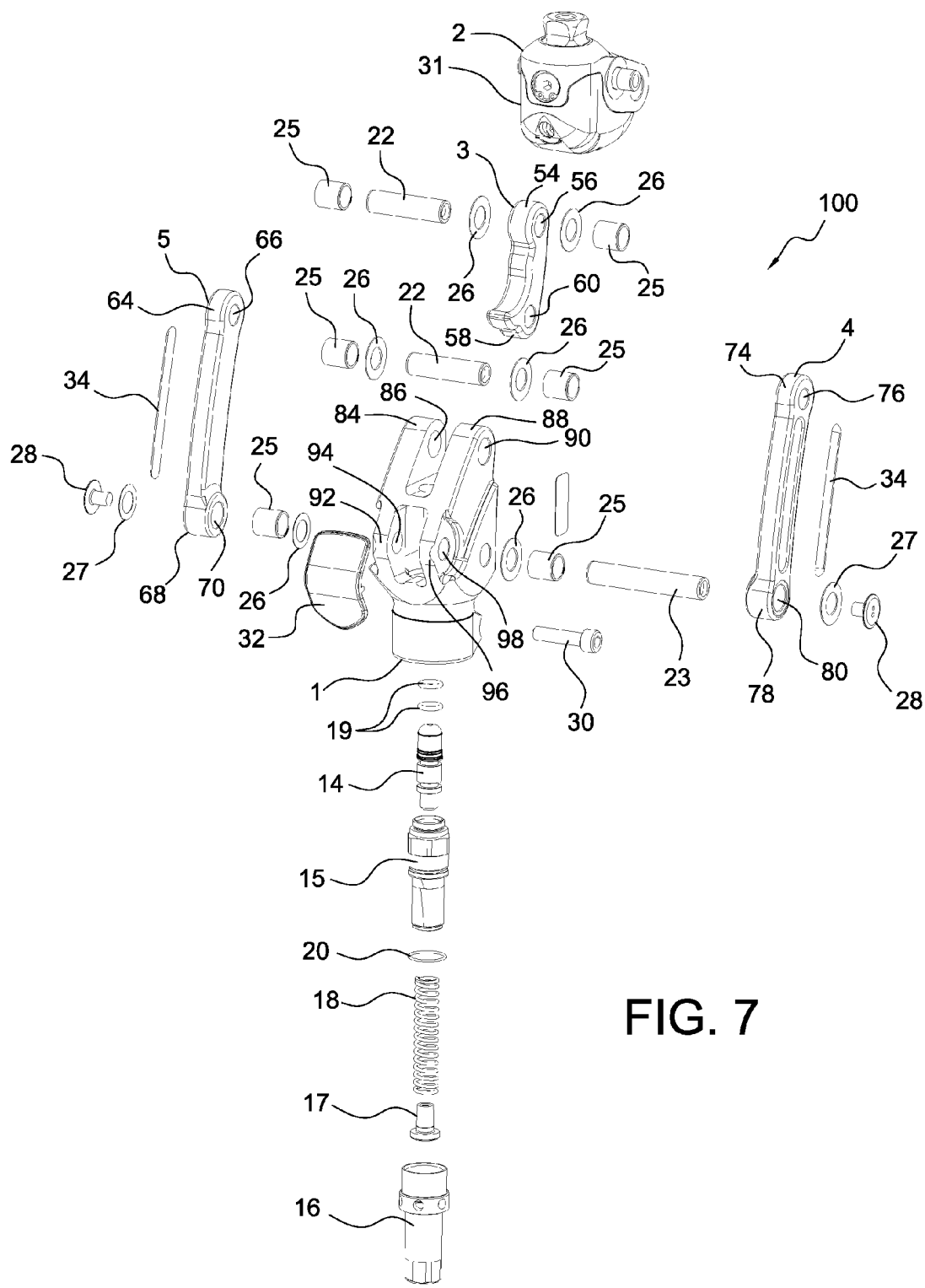
FIGS. 7 and 8 are exploded views of the prosthetic knee shown in FIG. 1.
Figure 8:
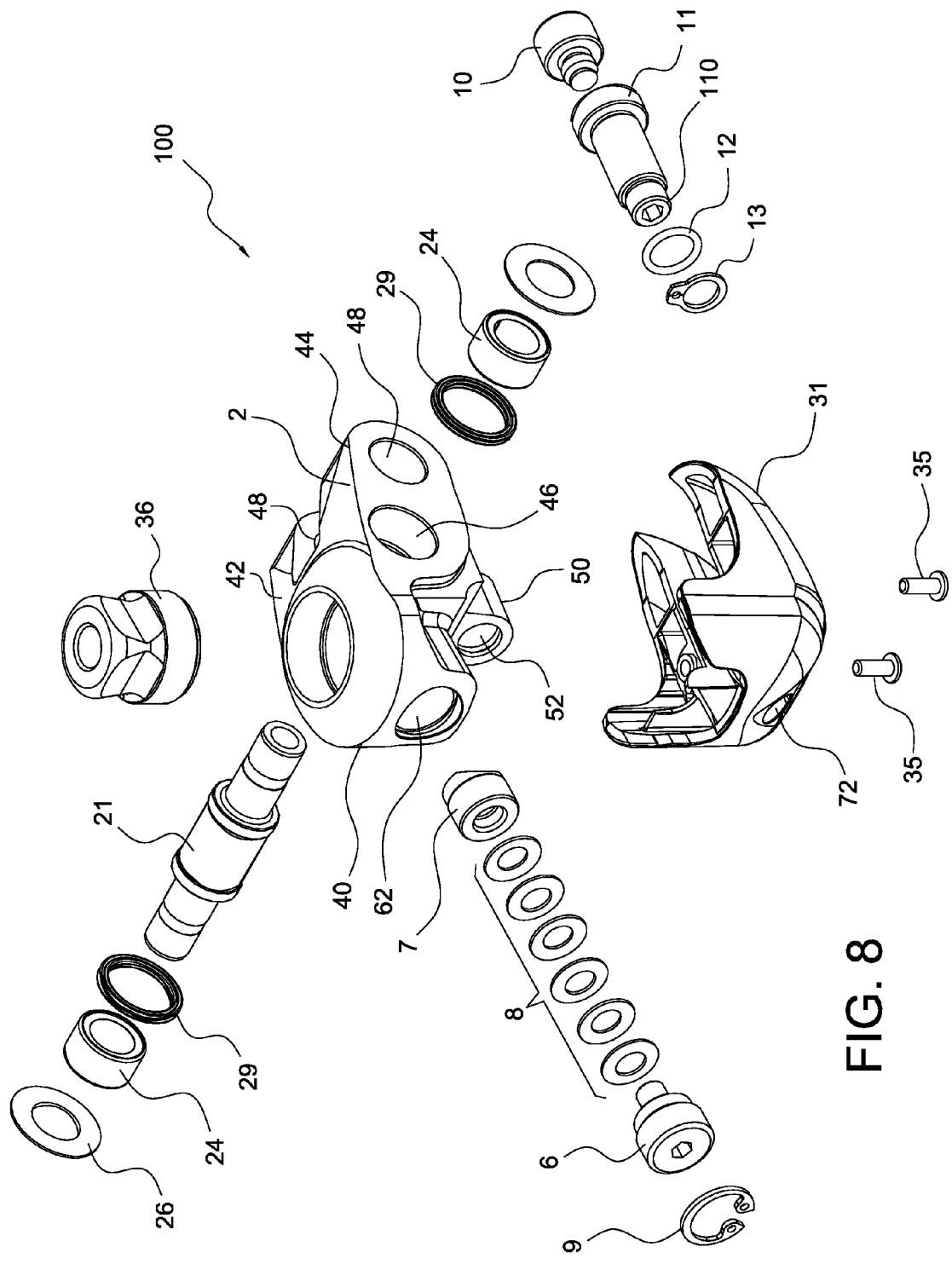

Turning back to FIG. 1, and as shown in FIGS. 7-8, the housing 2 includes a housing main body 40, with left and right flanges 42, 44 that protrude from the main body 40 towards the posterior. The left and right flanges 42, 44 are generally parallel to each other and each include a pivot pin hole 48. A pivot pin 22 is retained at each end by bearings 25 respectively positioned in the pivot pin holes 48.

The posterior link 3 has an upper end 54 that includes a pivot pin hole 56 passing therethrough. The upper end 54 of the posterior link 3 is positioned between the left and right flanges 42, 44, with the pivot pin 22 passing through the pivot pin holes 48 and pivot pin hole 56. Washers 26 are provided on the pivot pin 22 between the posterior link 3 and each of the left and right flanges 42, 44.

The housing main body 40 also includes a friction shaft pivot hole 46 passing therethrough, generally parallel to the pivot pin holes 48 and pivot pin hole 56. A friction shaft 21 passes through the friction shaft pivot hole 46, and the ends thereof extend beyond the housing main body 40. Seals 29 and needle bearings 24 are positioned on each end of the friction shaft 21 within the friction shaft pivot hole 46. Washers 26 are positioned on each end of the friction shaft 21 adjacent to the housing main body 40 and the anterior links 4, 5. The anterior links 4, 5 each define an upper end 64, 74 having a pivot pin hole 66, 76 passing therethrough, and the opposed ends of the friction shaft 21 are received in the upper pivot pin holes 66, 76.

As best seen in FIGS. 7-8, the friction shaft 21 includes an enlarged diameter portion within the housing main body 40 positioned between the opposed ends of the friction shaft 21. The enlarged diameter portion of the friction shaft 21 is provided to be used in the manner discussed below to provide constant friction and prevent excessive heel rise and terminal impact.

A friction screw hole 62 is provided at the anterior portion of the housing main body 40, generally perpendicular to, and communicating with the friction shaft pivot hole 46 to expose the enlarged diameter portion of the friction shaft 21.

Again, as best seen in FIG. 8, a depending protrusion 50 extends downwardly from a lower side of the housing main body 40, and has a hole 52 therein for holding and retaining a bumper holder 11, which is discussed in more detail below. The hole 52 is generally parallel to the friction screw hole 62. Both the friction screw hole 62 and the hole 52 are generally centrally aligned on the housing main body 40.

A knee cap cover 31 is positioned along the bottom side of the housing main body 40 and protects the housing main body 40, for example, while the user is kneeling. The knee cap cover 31 has an upper surface that is complementary shaped to the lower surface of the housing main body 40, including two parallel posterior flange portions, and two upright anterior portions. The upright anterior portions flank the friction screw hole 62 when the knee cap cover 31 is assembled with the housing main body 40. The knee cap cover 31 also includes an anterior hole 72 aligned with the hole 52 in the housing main body 40 to provide access to the hole 52 when the knee cap cover 31 is assembled with the housing main body 40. The knee cap cover 31 is assembled with the housing main body 40 and the assembly is retained together with screws 35. It will be recognized that alternative attachment mechanisms, such as bolts, rivets, adhesives, etc., or a combination thereof, may be used to secure the knee cap cover 31 to the housing main body 40.

As seen in FIGS. 1-4, the housing 2 and the chassis 1 are movably connected to each other by way of the anterior links 4, 5 and the posterior link 3.

Figure 6:
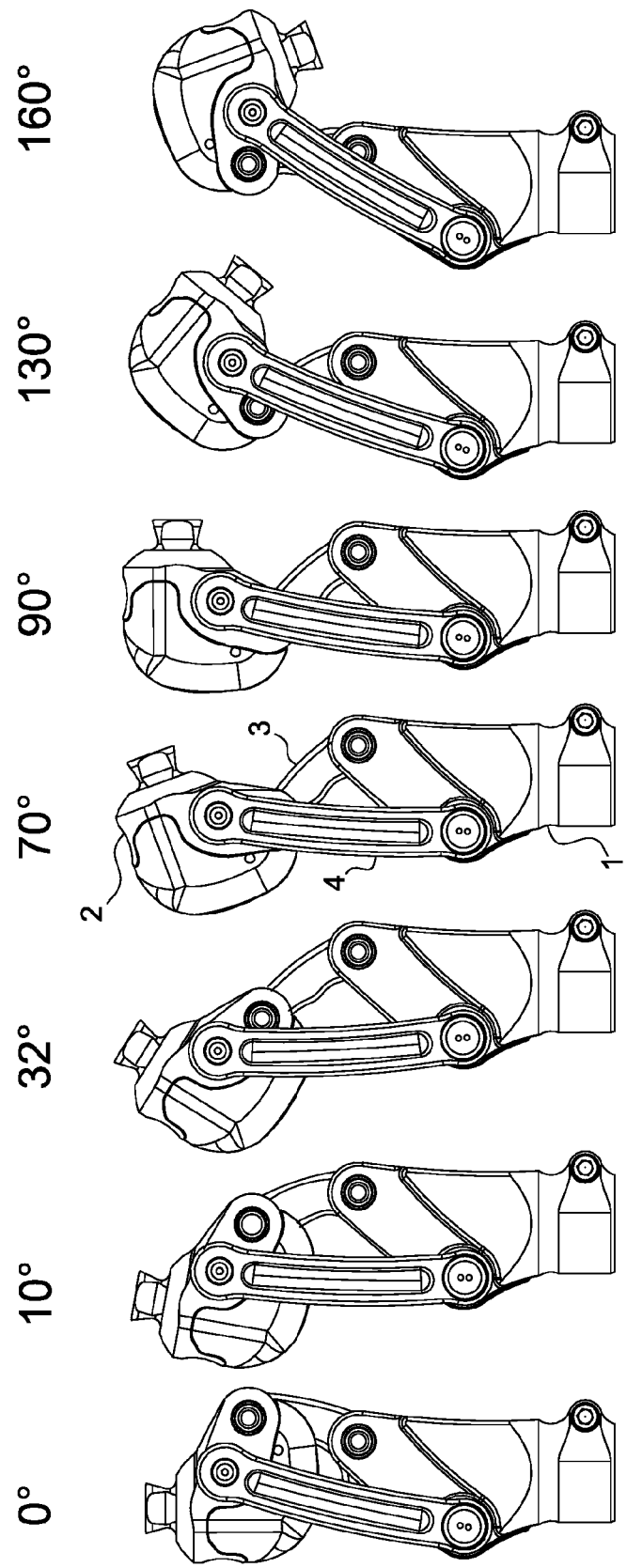
FIG. 6 is a right side view of the prosthetic knee shown in FIG. 1 and showing the relationship between the anterior and posterior links through 0 to 160 degrees of movement.

The relative relationships between the anterior links 4, 5 and posterior link 3 through 0 to 160 degrees of movement are shown in FIG. 6.

The structure of the links allows the housing 2 and the chassis 1 to be movably connected, and to move relative to one another as shown in FIG. 6 can best be seen in FIG. 7. Specifically, each of the anterior links 4, 5 have a lower end 78, 68 in which a pivot pin hole 80, 70 is provided. Similarly, the posterior link 3 also has a lower end 58, in which a pivot pin hole 60 is provided.

The chassis 1 has a corresponding structure, as discussed below, to which the lower ends 78, 68, 58 of the respective anterior and posterior links 4, 5, 3 are pivotally connected. The chassis 1 has a main body 82 with left and right upwardly extending and generally parallel flanges 84, 88. A pivot pin hole 86, 90 is provided in each of the flanges 84, 88 for receiving bearings 25 and opposed ends of a pivot pin 22, which passes through the pivot pin hole 30 in the posterior link 3.

Thus, as can best be seen in the back view of the prosthetic knee 100 shown in FIG. 3, the lower end 58 of the posterior link 3 is pivotally situated between the upwardly extending flanges 84, 88. Similarly to the upper end 54 of posterior link 3, as shown in FIG. 7, washers 26 are provided on the pivot pin 22 between the posterior link 3 and each of the upwardly extending flanges 84, 88.

Turning back to FIGS. 1 and 7, the main body 82 of the chassis 1 also includes two generally parallel anterior flanges 92, 96, each having a pivot pin hole 94, 98 formed therein. A pivot pin 23 extends through the pivot pin holes 94, 98, and into bearings 25 respectively received in each of the anterior link lower end pivot holes 70, 80. Bolts 28 and washers 27 are used to secure the lower ends 68, 78 of the anterior links 5, 4 to the pivot pin 23. A chassis cover 32 is provided to aid when the user is kneeling, and to prevent debris from accumulating on the pivot pin 23 where it is exposed between the flanges 92, 96.

Portions of the chassis 1 and the housing 2 are more easily seen in the back view shown in FIG. 3, including the tube clamp 128, a chassis access opening 126, and the left and right flanges 42, 44 of the housing 2. The chassis access opening 126 provides access to the extension assist mechanism, as discussed in more detail below FIGS. 4A and 4B illustrate a cross-sectional view of the prosthetic knee 100 taken along line 4-4 in FIG. 3, where FIG. 4A shows the prosthetic knee 100 at 0 degrees of flexion and FIG. 4B shows the prosthetic knee 100 at roughly 30 degrees of flexion. FIGS. 4A and 4B more clearly show the friction adjustment screw mechanism, the stability adjustment mechanism, and the extension assist mechanism.

In reference to FIGS. 3 and 4A-4B, the friction adjustment screw mechanism includes a friction adjustment screw 6, a friction pad 7, and the friction shaft 21. The friction adjustment screw mechanism provides constant friction and prevents excessive heel rise and terminal impact. For the friction adjustment mechanism, the friction shaft 21 extends into the friction shaft pivot hole 46 formed on the housing 2. The friction pad 7 is arranged within the friction screw hole 62 to engage the shaft 21 so as to adjust the friction of the shaft 21 when the friction adjustment screw 6 is turned. Turning the friction adjustment screw 6 in a first direction (tightening) increases the amount of friction on the friction shaft 21, and turning the friction adjustment screw 6 in a second direction (loosening) decreases the amount of friction on the friction shaft 21.

As seen in FIGS. 4A-4B and 8, friction adjustment screw 6 and friction pad 7 are connected to one another by Belleville washers 8 and a retainer snap ring 9. The Belleville washers 8, such as disc springs or spring washers, compensate for wear in the friction adjustment mechanism, particularly for swing control as in the instant knee 100. Alternative mechanisms for wear compensation include compression springs or other suitable biasing mechanisms. The retainer snap ring 9 allows for controlling the adjustment range, at least one end thereof, for the constant friction adjustment.

As also seen in FIGS. 4A-4B and 8 the stability adjustment mechanism includes a stability adjustment screw 110 connected to a bumper holder 11 for retaining an extension stop bumper 10. The stability adjustment mechanism is retained within the hole 52 in the depending protrusion 50 of the housing main body 40. An extension stop adjustment ring (retainer ring) 13 and a seal (O-ring) 12 are coaxially provided with the stability adjustment screw 110 and the bumper holder 11. The stability adjustment mechanism is a stability setting that balances between stability and dynamic behavior of the prosthetic knee. It allows the clinician to match the prosthetic knee to the needs and behavior of the wearer by tightening or loosening the stability adjustment screw 110, which alters the position of the extension stop bumper 10 as discussed in more detail below.

The retainer snap rings 9, 13 allow for the selection of how the user can adjust the knee and prevent inadvertent disassembly of the adjustment mechanism. Specifically, the retainer snap rings 9, 13 can be set by the clinician to limit the maximum amount of adjustment that can be made to the prosthetic knee 100 by the user.

Turning to FIGS. 4A-4B and 7, extension assist mechanism is shown. The extension assist mechanism includes the extension assist piston 14, which is retained in an inner housing 15, which remains fixed, along with an extension assist spring 18. Seals (O-rings) 19 are provided between the external surface of the extension assist piston 14 and the internal surface of the inner housing 15

The upper end of the inner housing 15 is held in a first hole 124 provided in the chassis main body 82 between the upwardly extending flanges 84, 88, so that the extension assist piston 14 can be biased into engagement with the lower end 58 of the posterior link 3, as discussed in detail below.

An adjustable external housing 16 is provided coaxially with the inner housing 15 and receives the inner housing 15 (and the extension assist piston 14) with seal (O-ring) 20 therebetween, as well as a spring guide 17 and the extension assist spring 18 therein. The spring guide 17 engages a bottom end of the extension assist spring 18, and the upper end of the extension assist spring 18 engages a bottom end of the extension assist piston 14. The adjustable external housing 16 is positioned within the chassis main body 82, extending into the tube portion of the tube clamp 128.

By accessing the adjustable external housing 16 through the access opening 126 (FIG. 3), a clinician can rotate the adjustable external housing 16 in the vertical direction (upwards or downwards) in order to alter the compression of the extension assist spring 18, and thus alter the biasing force applied to the extension assist piston 14 by the extension assist spring 18, and the biasing force applied to the posterior link 3 by the extension assist piston 14. In this manner, the extension assist mechanism allows for adjustment to the individual user's speed, by adjusting the outer housing.

A more detailed view of the interaction between the extension assist piston 14 and the posterior link 3 can be seen in FIG. 5, where alternate reference numerals are provided to identify specific features.

As shown in FIG. 5, the posterior link 114 includes an upper cam surface 118 and a lower cam surface 122 defined on a posterior link cam 121. The stability adjustment screw 110 is connected with the extension stop bumper 112 which has a rounded tip 116. The upper cam surface 118 is convex relative to the tip 116 which allows for a consistent and smooth surface contact for the extension stop bumper 112 to strike, thereby easing use of the prosthetic knee as it enters maximum extension and reducing any noise. The lower cam surface 122 is concave relative to the piston 120 thereby providing consistent and smooth surface contact between the piston 120 and the posterior link 114.

FIGS. 4A-4B show the interaction between the posterior link cam surfaces and the extension stop bumper and extension assist piston between 0 degrees and roughly 30 degrees flexion. In the exemplary embodiment, the extension assist mechanism provides extension assist between 0 degrees and 70 degrees flexion.

As shown in FIG. 7, an anterior link sticker 34 may be provided on the side anterior links 4, 5 for decorative and/or protective purposes.

A shin ferrule may be used to provide cosmetic finishing and also protect the knee from wear and tear.

C. Locking Mechanism Embodiments

According to the embodiment of FIGS. 9A-9E, a locking mechanism 200 is provided in which a pin lever 210 spring loaded by a coiled spring is adapted to selectively rotate a pin 202 which locks the posterior link 103 in place or permits it freely rotate. A set screw 216 is used to position the locking mechanism in position.

Figures 9A, 9B:
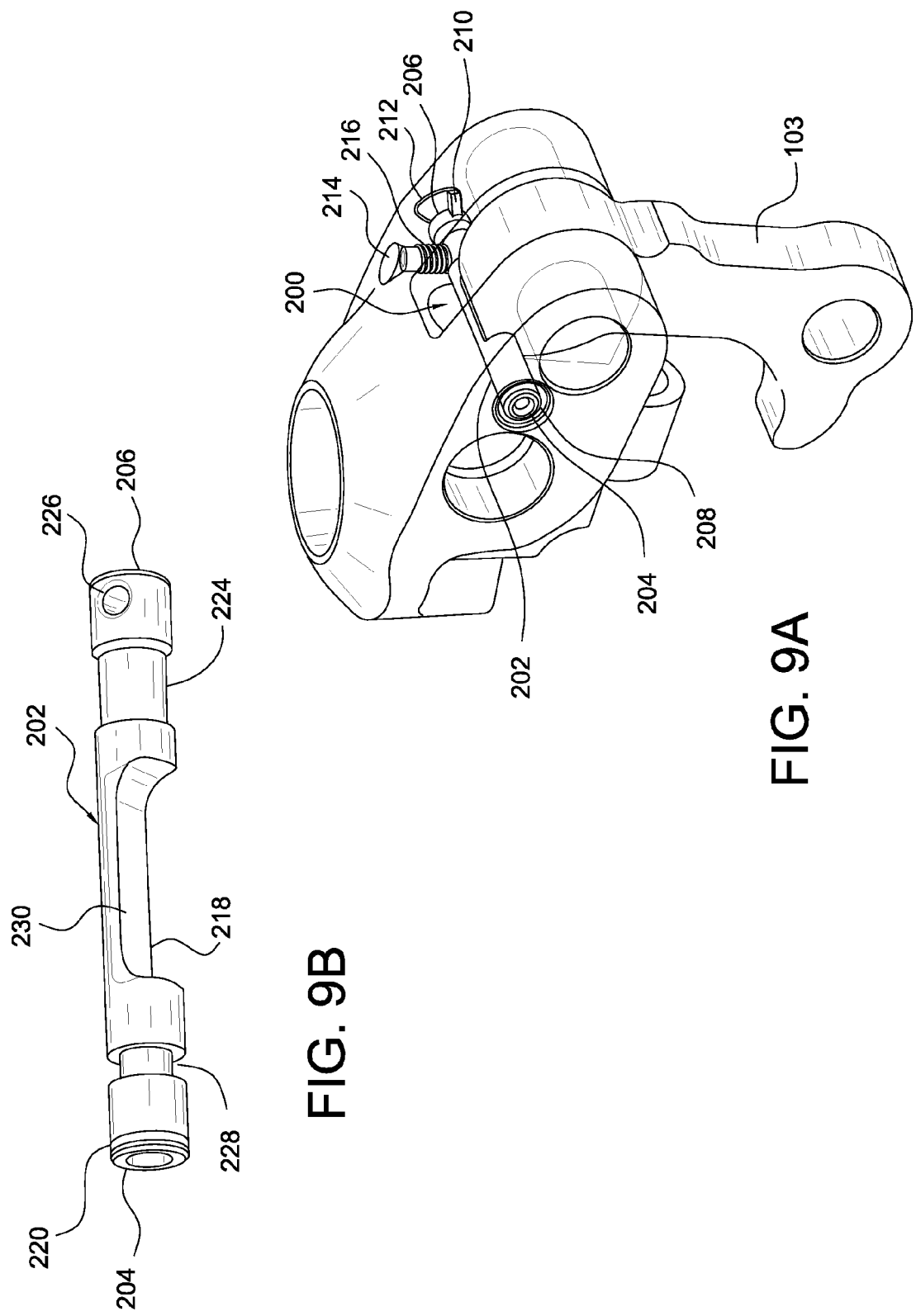
FIG. 9A is a perspective view of a locking mechanism.
FIG. 9B is a perspective view of a locking pin for the mechanism of FIG. 9A.

In reference to FIG. 9A, the pin 202 extends through and is rotatable relative to a portion of the housing 104 and is in engagement with the posterior link 103. A first end of the pin 204 is secured by a clip 208 so as to prevent it from slipping from the housing. A second end of the pin 206 is secured to the pin lever 210. The pin lever 210 is pivotable in a recess 212 formed by the housing. A set screw 216 movably extends into an opening 214 of the housing 104, and is generally arranged perpendicularly to the pin 202 so as to engage therewith.

An embodiment of the pin 202 is shown in FIG. 9B, wherein the first end 204 of the pin has a groove 220 that is adapted to receive the clip. The pin 202 defines an elongate recess 218 having a generally flat surface 230 for engaging a notch on the posterior link 103. The pin 202 also defines a generally circumferential groove 224 adjacent the second end of the pin 202 for receiving the set screw 216. The second pin end also includes an aperture 226 for receiving the pin lever 210.

FIGS. 9C-9E show various stages of adjustment of the pin lever. In observing FIG. 9C, the locking mechanism is in a locked configuration whereby the pin engages the posterior link, and the set screw is tightened against the pin. The posterior link 103 has a notch 232 with upper and lower surfaces 234, 236 that correspond to the recess 218 of the pin 202 such that the lower surface 236 is generally parallel to the surface 230. The notch 232 effectively engages the pin 202, and prevents rotation of the posterior link 103.

FIG. 9D depicts the locking mechanism as it is prepared for an unlocked configuration. Specifically, the set screw 216 is loosened so as to allow for rotation of the pin. The pin 202 is turned by the practitioner by the lever 210, which in turn permits rotation of the posterior link 103, and the pin 202 clears the way for the posterior link 103 to rotate.

According to FIG. 9E, once rotation of the posterior link 103 is permitted, the set screw 216 is tightened to maintain position of the pin in an unlocked configuration so as to permit rotation of the posterior link 103.

Figure 10A:
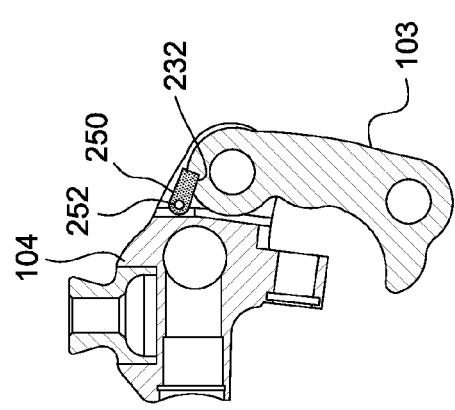
FIG. 10A is detailed view showing another locking mechanism in a locked configuration.
Figure 10B:
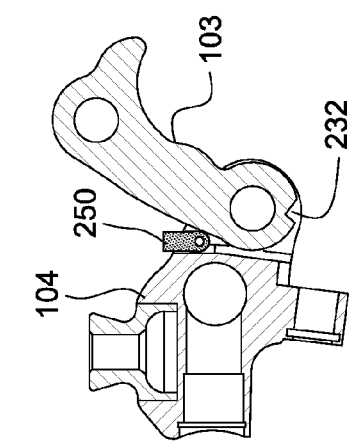
FIG. 10B is a detailed view showing the mechanism of FIG. 10A in an unlocked configuration.

FIGS. 10A and 10B illustrate another locking mechanism embodiment. In this embodiment, a spring loaded latch 250 pivotable about point 252 is accessible from the top exterior portion of the housing 104 (similar to the following embodiment of FIGS. 12A-12C). The latch 250 is biased between locked and unlocked positions such that when in the locked configuration of FIG. 10A, the latch 250 engages the notch 232 on the posterior link, and in the unlocked configuration of FIG. 10B, the latch 250 is flipped up from the notch 232 to permit rotation of the posterior link 103.

Figure 11A:
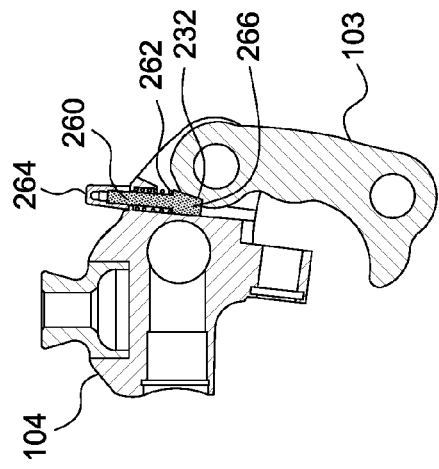
FIG. 11A is a detailed view showing another locking mechanism in a locked configuration.
Figure 11B:
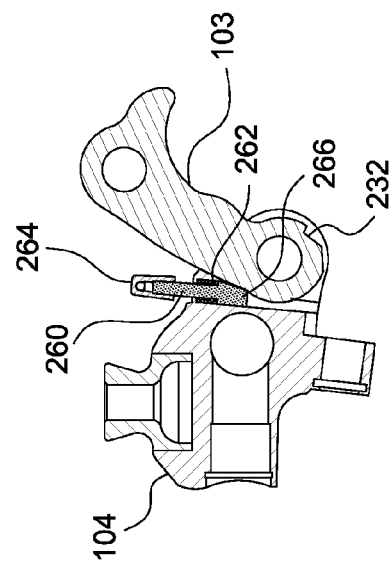
FIG. 11B is a detailed view showing the mechanism of FIG. 11A in an unlocked configuration.

FIGS. 11A and 11B depict another locking mechanism embodiment. According to this embodiment, a locking pin 260 is spring loaded by spring 262 which prevents the posterior link 103 from moving and biases a pin head 266 of the pin 260 to engage the notch 232, as show in FIG. 11A in the locked configuration. FIG. 11B depicts the locking mechanism in an unlocked configuration wherein the locking pin 260 is pulled by handle 264 away from the notch in order to unlock the posterior link and allow knee flexion.

Figure 12A:
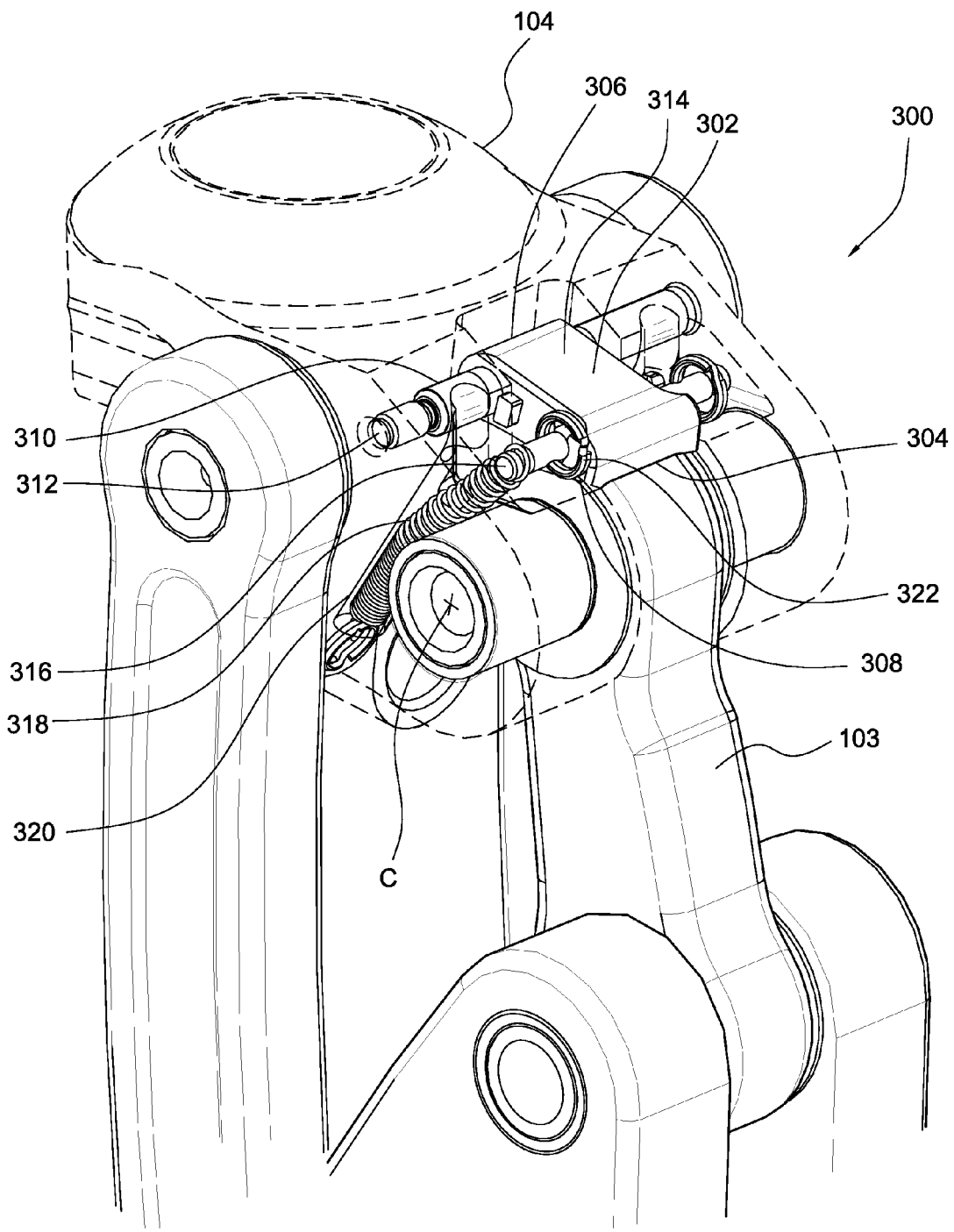
FIG. 12A is a perspective view showing another locking mechanism in a locked configuration.
Figure 12B:
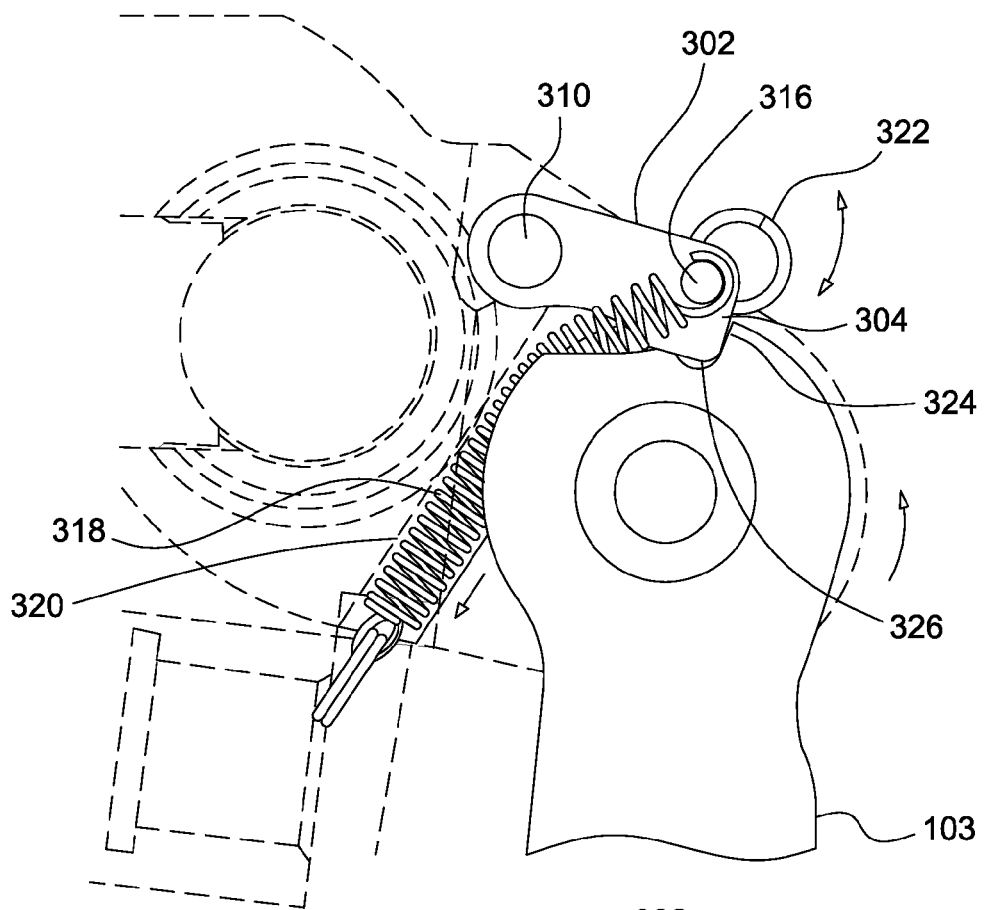
FIG. 12B is a detailed view showing the mechanism of FIG. 12A in a locked configuration.
Figure 12C:
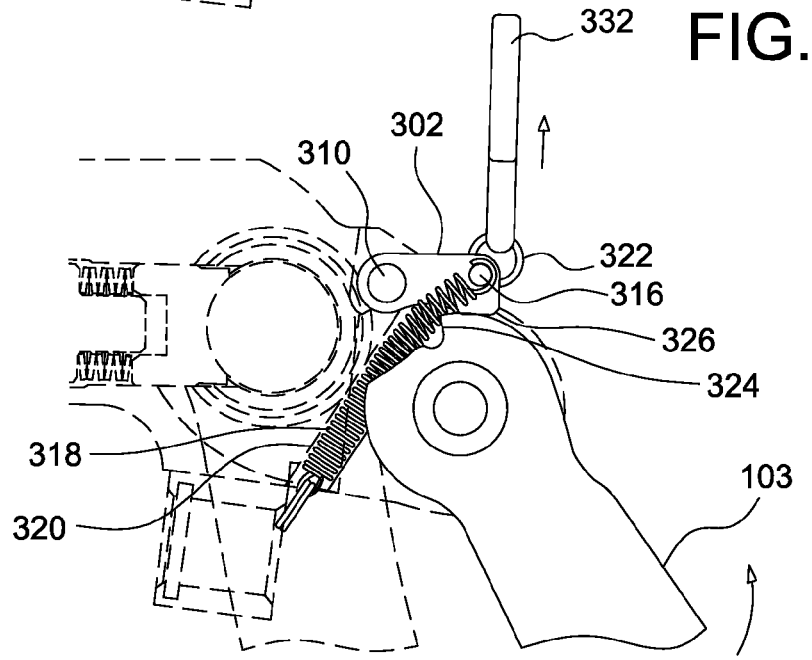
FIG. 12C is a detailed view showing the mechanism of FIG. 12A in an unlocked configuration.

FIGS. 12A-12C show another embodiment of a locking mechanism. In this embodiment, a latch 302 is secured to an axle 310 rotatable within an opening 312 in the housing 104. The latch 302 has a rearward end 306 that is received by a recess 314 that is formed by the housing 104, and a forward end 304 that is engageable with a notch 324 formed by the posterior link 103. A pair of springs 318, such as elongate coil springs, are connected to the housing 104 and secured therein 320 are secured to a pin 316 engaging the forward end 304 of the latch 302. Attachment elements 322 are mounted on the pin 316 in order to provide a connection for a lanyard or other suitable connection element used for pulling the latch 302.

FIG. 12B shows the locking mechanism 300 in a locked configuration. In this configuration, the latch forward end 304 has a nose portion 326 engages the notch 324. The latch 302 is biased to engage the notch 324 by the springs 318. The line of action of the latch contact with the posterior link is such that the locking mechanism remains locked under external loading on the knee. FIG. 12C depicts the locking mechanism 300 in an unlocked configuration, wherein a lanyard 332 attaches to the elements 322, and is used to pull the nose portion 326 from the notch 324, to disengage the latch 302 from the notch, and thereby allow rotation of the posterior link 103. The latch 302 is configured to have sufficient clearance so as to allow for complete flexion of the knee.

Figure 13A:
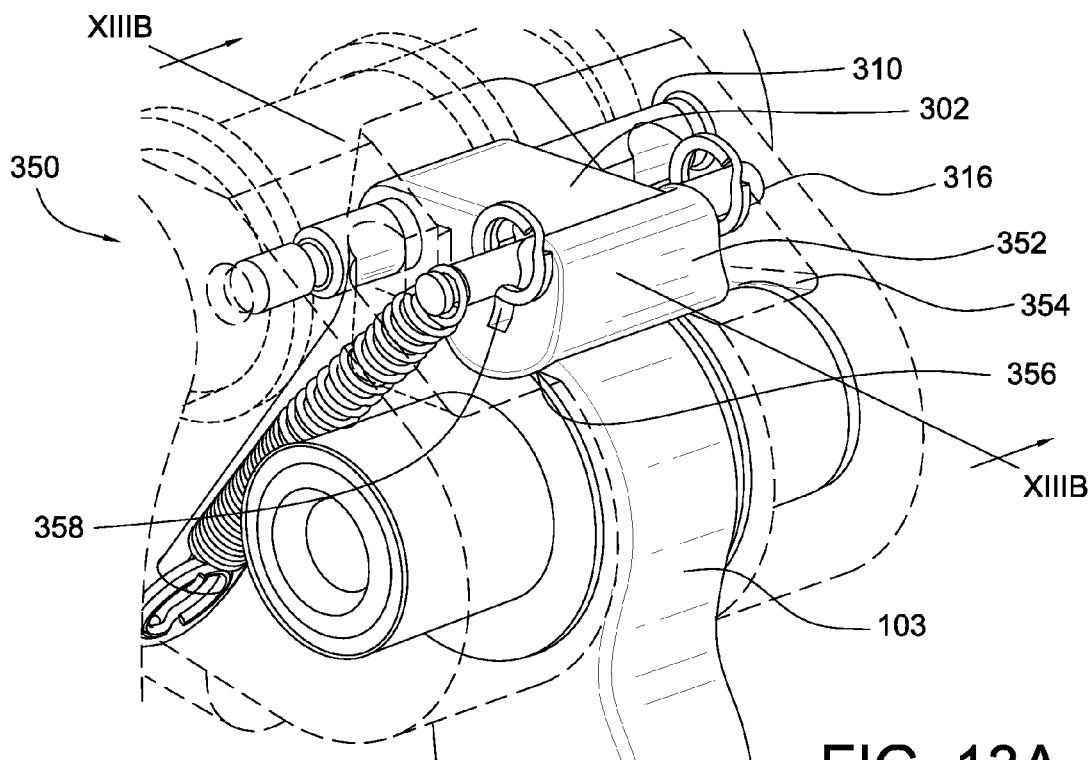
FIG. 13A is a perspective view showing the mechanism of FIG. 12A including a block element.
Figure 13B:
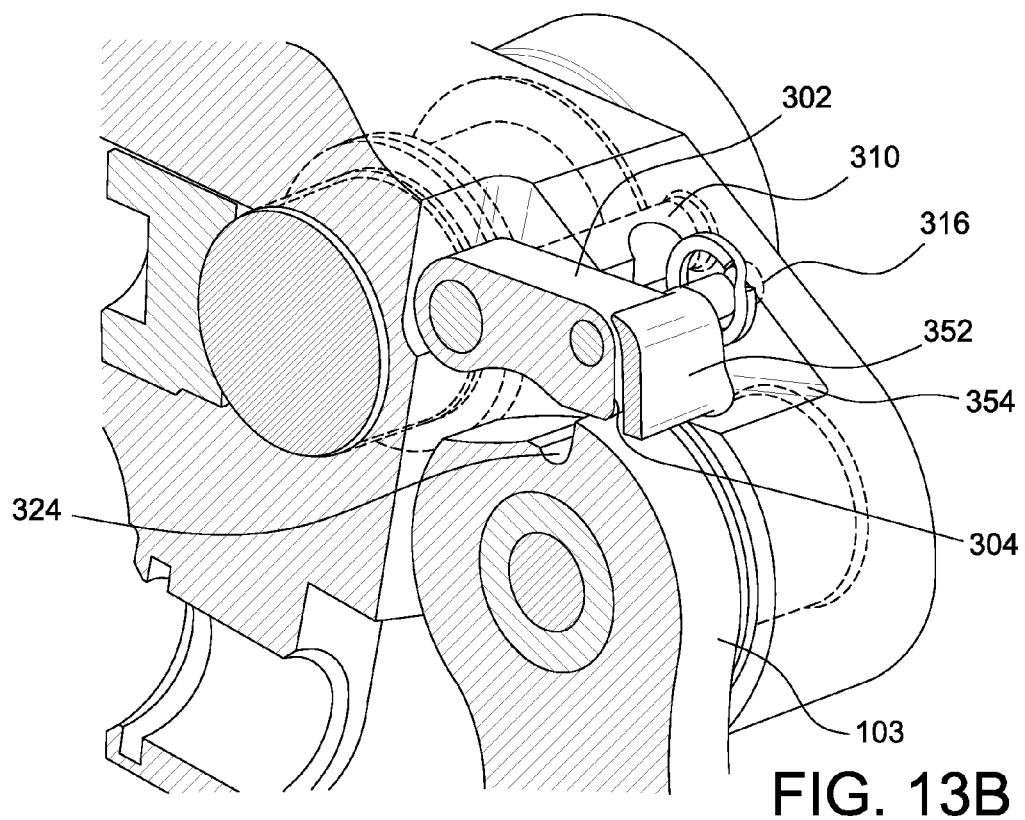
FIG. 13B is a cross-sectional view taken along line XIIIB-XIIIB in FIG. 13A.

FIGS. 13A and 13B show a variation of the embodiment of FIGS. 12A and 12B that includes a block element 352 for maintaining the knee in an unlocked configuration. According to this embodiment, the block element 352 attaches to the forward end 304 of the latch 302 by attaching to the pin 316 by a notched recess 358 that snaps onto the pin 316, and corresponds to the latch forward end 304. The block element 352 has a head portion 352 that prevents the latch forward end 304 from engaging the notch 324. Once secured onto the pin 316, the block element 352 thwarts the forward end 304 from engaging the notch 324.

The lock prevent element has the advantage of allowing a practitioner to make the knee so that the wearer can walk on an unlocked knee, and thereby remove the possibility of the lock from engaging the posterior link.

D. Conclusion

It will be recognized that the prosthetic knee and components thereof can be made from any suitable materials.

For example, the components can be constructed from an appropriate material such as those capable of providing lightweight structural support. Examples of such materials include, but are not limited to, plastics, steel alloys, aluminum alloys, other metals, ceramics, or other rigid materials. In an exemplary embodiment, the knee cap cover 31, as well as the chassis cover 32, may be made from suitable molded plastics. Additionally, in the exemplary embodiment, the chassis 1, housing 2, anterior links 4, 5, and posterior link 3 may be made from machined Aluminum (2024), and may anodized, for example, black or grey. Further, in the exemplary embodiment, the extension stop bumper can be made of rubber and the extension spring can be made from spring steel.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features from the disclosed embodiments and variations. In addition to variations described herein, other known equivalents for each feature can be mixed and matched by one of ordinary skill in the art to construct a prosthetic knee in accordance with principles of the present invention.

Although this invention has been disclosed in the context of exemplary embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

What is claimed is:

1. A prosthetic knee, comprising:
   a pair of anterior links;
   a posterior link defining a notch;
   a housing having a main body and right and left flanges extending in a posterior direction from the main body, the housing connecting the pair of anterior links and the posterior link, the anterior links connected to the housing at first upper pivot points, and the posterior link connected to the housing between the right and left flanges at a second upper pivot point;
   a chassis connecting the pair of anterior links and the posterior link, the anterior links connected to the chassis at first lower pivot points, and the posterior link connected to the chassis at a second lower pivot point, wherein the posterior link extends between a rear side of the housing and a rear side of the chassis;
   a locking mechanism connected to the housing and arranged to block rotation of the posterior link about the second upper pivot point by selectively engaging the notch of the posterior link, the locking mechanism including a latch having a rearward end received in a recess defined by the housing and a forward end engageable with the notch of the posterior link, and a pair of elongate springs extending downwardly from the latch to the housing, the springs being connected to the housing below the second upper pivot point and to a pin engaging the forward end of the latch.

2. The prosthetic knee of claim 1, wherein the latch is pivotable about a point and accessible from a top exterior portion of the housing.

3. The prosthetic knee of claim 2, wherein the latch is secured to an axle rotatable within an opening in the housing, the axle defining the point.

4. The prosthetic knee of claim 1, further comprising attachment elements mounted on the pin to provide a connection for a connection element used for pulling the latch.

5. The prosthetic knee of claim 1, wherein in a locked configuration, a lanyard is attached and arranged to pull the forward end from the notch to disengage the latch from the notch, and thereby allow rotation of the posterior link.

* * * * *